United States Patent
Zwaal

(10) Patent No.: US 8,553,654 B2
(45) Date of Patent: Oct. 8, 2013

(54) METHOD FOR EXPRESSION EVALUATION AND NETWORK NODE IMPLEMENTING SUCH A METHOD

(75) Inventor: Hugo Zwaal, Breda (NL)

(73) Assignee: Telefonaktiebolaget L M Ericsson (publ), Stockholm (SE)

( * ) Notice: Subject to any disclaimer, the term of this patent is extended or adjusted under 35 U.S.C. 154(b) by 719 days.

(21) Appl. No.: 12/666,083

(22) PCT Filed: Jun. 27, 2007

(86) PCT No.: PCT/NL2007/050309
§ 371 (c)(1),
(2), (4) Date: Jan. 11, 2010

(87) PCT Pub. No.: WO2009/002147
PCT Pub. Date: Dec. 31, 2008

(65) Prior Publication Data
US 2010/0329219 A1   Dec. 30, 2010

(51) Int. Cl.
*H04J 3/00* (2006.01)
*H04B 7/00* (2006.01)

(52) U.S. Cl.
USPC .......................................... 370/336; 455/512

(58) Field of Classification Search
USPC .................... 370/328, 329, 326, 331, 333; 455/37–439
See application file for complete search history.

(56) References Cited

U.S. PATENT DOCUMENTS 7,430,427 B2 * 9/2008 Briancon et al. .............. 455/512

FOREIGN PATENT DOCUMENTS

WO         00/03550       1/2000
WO    WO 00/03550    *  1/2000

OTHER PUBLICATIONS

Chakravarthy, S. et al. "ECA Rule Integration into an OODBMS: Architecture and Implementation." Proceedings of the 11th International Conference on Data Engineering, 1995. Taipei, Taiwan, Mar. 6-10, 1995, pp. 341-348.

* cited by examiner

*Primary Examiner* — Afshawn Towfighi
(74) *Attorney, Agent, or Firm* — Coats and Bennett PLLC

(57) ABSTRACT

Method and network node (2) for a communication network (1) providing a service in the communication network. The network node (2) is arranged to communicate with 5 context sources (12, 15, 16) providing input values for a triggered expression evaluation, and to provide a network service to communication devices (12, 15, 16) based on the result of the triggered expression evaluation. An evaluation result of the triggered expression evaluation is obtained upon a change to an input value, and the triggered expression evaluation comprises the evaluation of nodes in an expression 10 graph. Each internal node is assigned a priority based on the level of the node in the expression graph. Actual reception of a trigger by an internal node is scheduled based on the priority of the internal node, such that the internal node will only receive a trigger after internal nodes with a higher priority have received their associated triggers.

14 Claims, 4 Drawing Sheets

METHOD FOR EXPRESSION EVALUATION AND NETWORK NODE IMPLEMENTING SUCH A METHOD

FIELD OF THE INVENTION

The present invention relates to a method for expression evaluation, which is used in many technical applications, such as context source evaluations in mobile network based services, but also in sensor network applications (e.g. in automotive industry) or logic circuitry. More in particular, the present application relates to method for triggered expression evaluation upon a change to an input value.

PRIOR ART

Expression evaluation is normally done in a top-down fashion. When the value of an expression needs to be evaluated, all operands are evaluated left-to-right in a depth-first manner. Triggered expression evaluation, however, is performed bottom-up. This means that an expression is re-evaluated whenever the value of one of its operands changes. Since the expression can be an operand itself, the changes will propagate towards the top-most expression(s). Triggered expression evaluation is typically implemented by having an operand trigger its parent (higher level) expression(s), which then re-evaluate their value(s) and in turn trigger their parent(s) if a change is detected.

SUMMARY OF THE INVENTION

In a method according to the prior art, such an implementation exhibits the following problem, since only one parent expression can be re-evaluated at a certain moment.

When multiple parallel paths from an operand exist toward the same ancestor, the triggers (for the same change) along these different paths might cause a temporarily incorrect expression result.

The present invention seeks to provide a method which eliminates this type of problem during triggered expression evaluation.

According to the present invention, a method as defined above is provided, in which the triggered expression evaluation comprises the (consecutive) evaluation of nodes in an expression graph, the expression graph having nodes and one or more triggers from a sending node to a receiving node, the nodes being an external node or an internal node, an external node comprising an input value and providing an external trigger upon a change of the input value, an internal node comprising an expression (i.e. a logical, Boolean operation, etc.) on one or more operands, each of the one or more operands comprising a trigger caused by a sending node, each internal node being assigned a priority based on the level of the node in the expression graph, the method further comprising scheduling actual reception of a trigger by an internal node based on the priority of the internal node, such that the internal node will only receive a trigger after internal nodes with a higher priority (=lower level) have received their associated triggers. Each node may provide a trigger for a receiving (i.e. higher level) node, or it may provide an end result of the expression evaluation. With this embodiment, in which the reception rather than sending of triggers is controlled, and in which triggers of internal nodes are handled based on the priority of the receiving node, allows to prevent possible errors due to a multipath problem.

A graph having nodes and branches is a well known general term in network technology. Other terms may be used to describe similar entities, e.g. a tree having branches and leaves.

In a further embodiment, an internal node obtains a priority that is lower than the lowest priority of the sending nodes of associated operands. This provides for an efficient and robust prioritization scheme, in which nodes closer to the external node (input value monitored) are handled first. In an exemplary implementation, the internal nodes may be assigned levels according to their position in the graph, in which the internal nodes closer to the external nodes obtain a higher priority (=lower level).

An implementation embodiment uses an internal queue in which a trigger is entered in a prioritized order using the priority of the node receiving the trigger. From the queue, the trigger with the highest associated priority is taken out of the queue first (or positioned at the top of the queue in front of other triggers having a lower priority).

With triggered expression evaluation, a further problem may arise when multiple input values change (almost) simultaneously. The external triggers caused by these changes may interfere somewhere in the expression graph and provide an erroneous end result. To solve this problem, in a further embodiment of the invention, external triggers are only scheduled when no internal triggers exist (e.g. when no internal triggers are in the internal queue). In a further embodiment, external triggers are scheduled with a lowest priority. In that manner, external triggers are always handled last, after any other pending internal triggers. In a further embodiment, external triggers are entered in an external trigger queue (separate from the internal trigger queue), which is handled in a first-in-first-out manner, but only when the internal queue is empty.

In a further aspect, the present invention relates to a network node for a communication network providing a service in the communication network, in which the network node is arranged to communicate with context sources providing input values for an expression evaluation, and to provide a network service to communication devices based on the result of the expression evaluation, in which the network node is further arranged as described in claims 8-13.

In an even further aspect, the present invention relates to a processing circuit comprising one or more input units, an output unit, and logic circuitry connected to the one or more input units and output unit, in which the logic circuitry implements a set of logical expressions for triggered expression evaluation using the input units to obtain input values and the output unit to provide an evaluation result, further comprising a logic circuitry control unit for controlling the order of expression evaluation in the set of expressions according to any one of the method embodiments.

SHORT DESCRIPTION OF DRAWINGS

The present invention will be discussed in more detail below, using a number of exemplary embodiments, with reference to the attached drawings, in which FIG. 1 shows a schematic diagram of a communication network in which the present invention may be embodied;

DETAILED DESCRIPTION OF EXEMPLARY EMBODIMENTS

Figure 1:
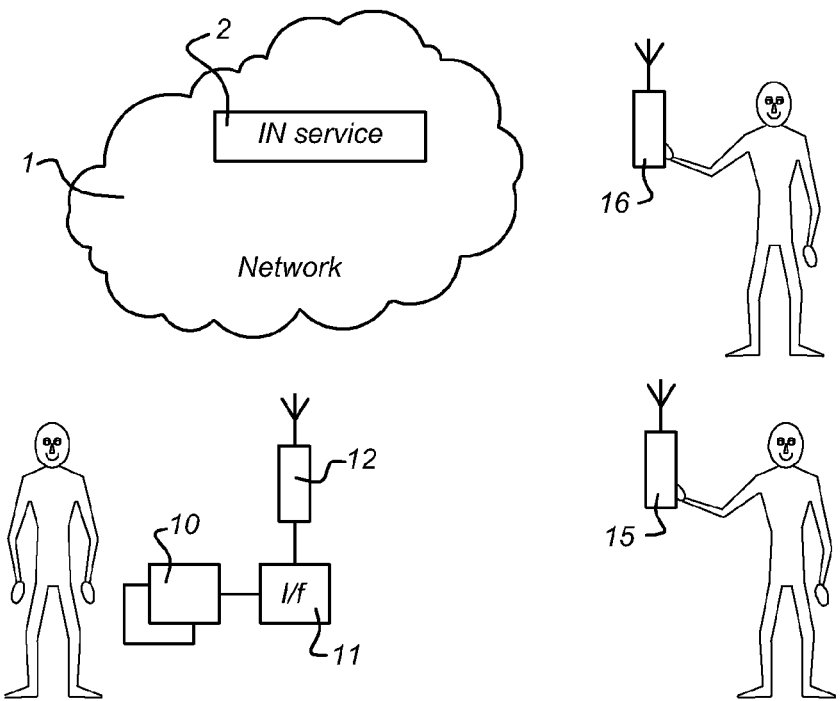

The present invention embodiments, as described in the annexed claims, are clarified below using an example of an expression evaluation for a mobile network service. A heart monitoring system or service may e.g. be implemented as a service in an intelligent (mobile) communication network 1, where a heart patient is monitored (using sensors 10, a sensor interface 11, and a (mobile) communication device 12) and a caretaker needs to be notified as soon as an abnormal heart condition occurs (e.g. using a mobile communication device 15, 16). This is illustrated schematically in FIG. 1, which shows the communication network 1 comprising an intelligent network node 2 which executes an intelligent network service (service layer execution). The patient is shown with a number of sensors 10, which are connected to a mobile station 12 using a sensor interface 11. On the other side, caretakers are shown (e.g. a nurse and a doctor) with associated mobile stations 15, 16. The mobile stations 12, 15, 16 may be provided with location devices, such as GPS receivers, which allow the mobile station to determine its position. As an alternative, the network 1 is arranged to determine the locations of the mobile stations 12, 15, 16, e.g. using radio triangulation.

The monitoring system, which may e.g. be implemented in the intelligent network node 2 in the mobile (tele)communications network 1, can be illustrated using a few simple expressions:

HeartrateAlarm:=Patient.Heartrate>150;

BloodpressureAlarm:=Patient.Bloodpressure>100;

Alarm:=BloodpressureAlarm OR HeartrateAlarm;

MajorAlarm:=BloodpressureAlarm AND HeartrateAlarm;

MinorAlarm:=Alarm AND NOT MajorAlarm;

NurseDistance:=DIST(Patient.Location,Nurse.Location);

NurseCanHelp:=Nurse.Available AND(NurseDistance<10);

NurseCannotHelp:=NOT NurseCanHelp OR NOT MinorAlarm;

NotifyNurse:=MinorAlarm AND NurseCanHelp;

NotifyDoctor:=Alarm AND Doctor.Available AND NurseCannotHelp;

The input values used in the monitoring system (e.g. Patient.HeartRate) can be seen as context sources for the service implemented in the intelligent network service node 2.

In plain words, the above set of expressions results in that in case of a minor alarm (one heart parameter over threshold) a nurse is notified when available and within reasonable distance. In case of a major alarm (both heart parameters over threshold) or when a nurse cannot help, a doctor is notified when available.

Figure 2:
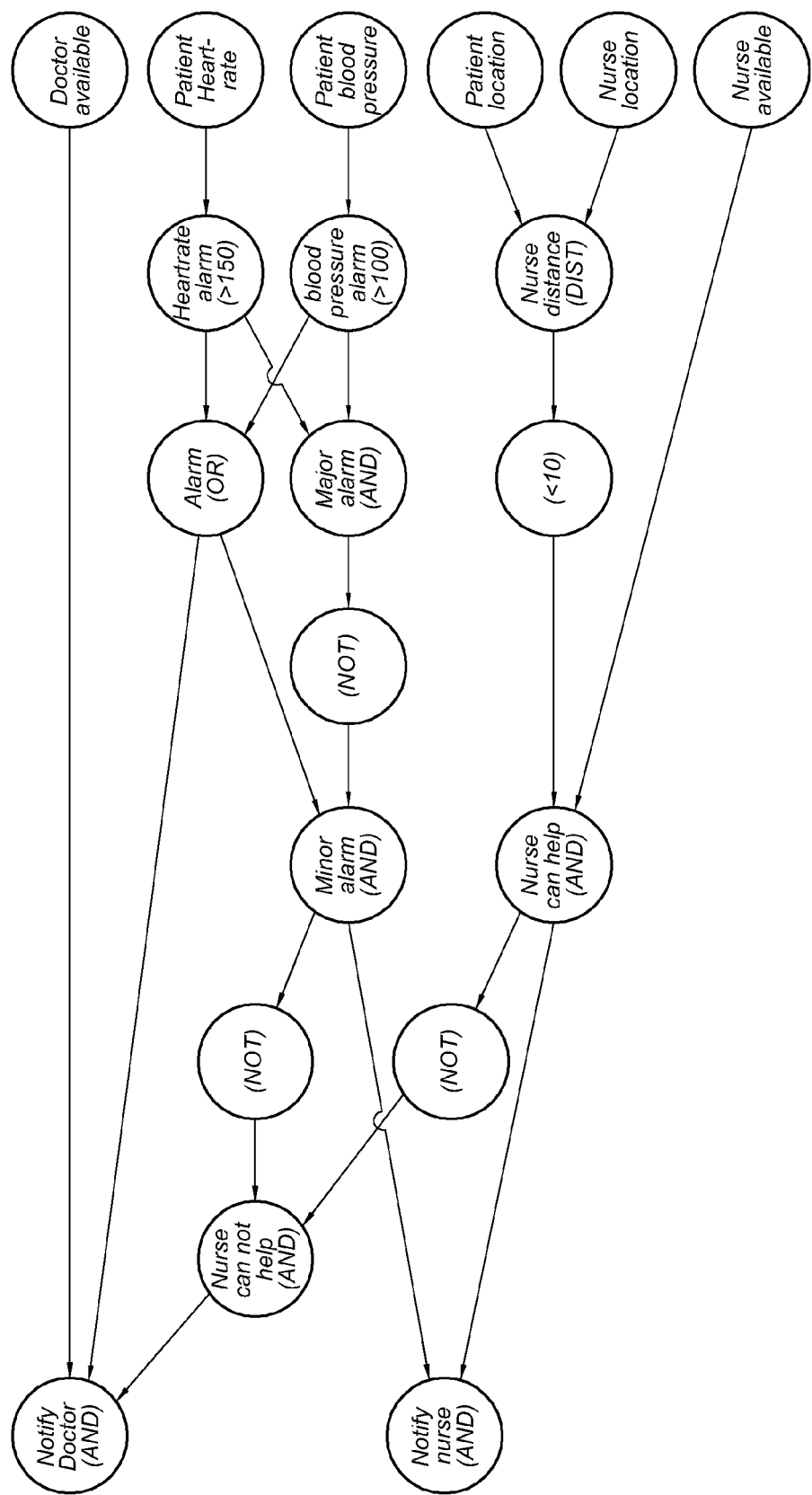
FIG. 2 shows a graph representation of an expression evaluation example.

The above set of expressions can also be represented visually in a graph, as shown in FIG. 2 (note that in triggered expression evaluation, evaluation is bottom-up (right to left in FIG. 2, hence the arrows which indicate the trigger direction).

Each of the expressions in the set of expressions (and possible intermediate expressions) are indicated by internal nodes, which receive triggers (one way branches between a sending node and a receiving node). Each node thus represents a single expression, which is a (logical, Boolean, . . . ) operation on one or more operands (the received triggers). The internal node possibly provides a trigger for a higher level (parent) node in the graph. The top-most internal nodes not providing a further trigger (i.e. not having any parent nodes in graph terminology) are the results of the expression evaluation (e.g. Notify Nurse and Notify Doctor in the example of FIG. 2).

The input values for the set of expressions (the external changing variables, or context sources), are indicated as rightmost nodes, or external nodes in the graph of FIG. 2, e.g. the Patient.Heartrate. These external nodes are trigger based, and can provide a trigger when an input value changes.

Triggered expression evaluation is typically implemented by having an operand trigger its parent (higher level) expression(s), which then re-evaluate their value(s) and in turn trigger their parent expression(s) if a change is detected. Since only one parent can be re-evaluated at a certain moment, such an implementation exhibits the following two problems.

When multiple parallel paths from an operand exist toward the same ancestor, the triggers (for the same change) along these different paths might cause a temporarily incorrect expression result, as indicated in the following example.

Figure 3:
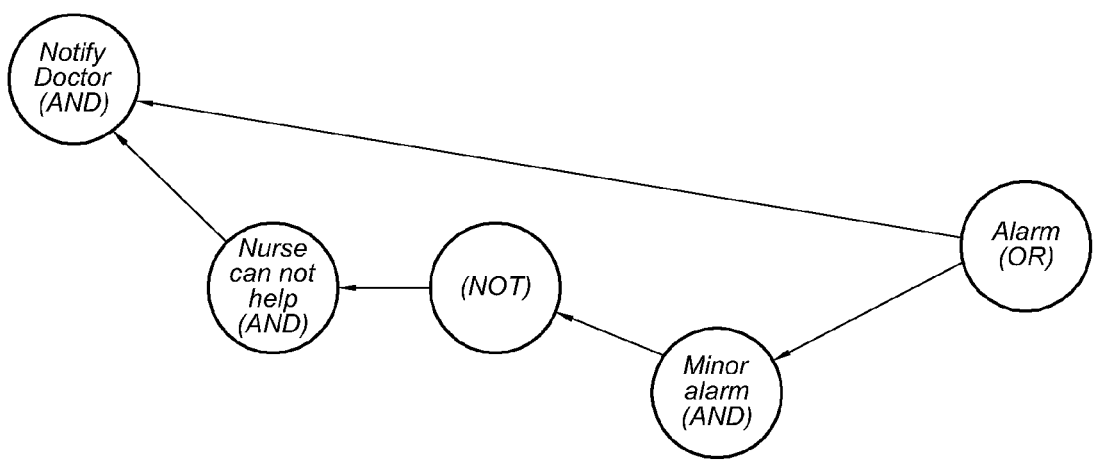
FIG. 3 shows a part of the graph of FIG. 2 illustrating a multipath example.

In the heart monitoring example, two parallel paths exist between the Alarm and NotifyDoctor nodes. These paths are visualized in FIG. 3 (for clarity, the rest of the expression graph has been omitted).

Consider the situation in which the Patient.Heartrate exceeds the threshold (150) and a HeartrateAlarm is detected and both the doctor and the nurse are available. The HeartrateAlarm is re-evaluated (to true) and its parents (Alarm and MajorAlarm) are triggered.

Alarm and MajorAlarm both are re-evaluated (sequence does not matter here, Alarm changes to true and MajorAlarm stays false) and the Alarm change is detected and its parents (NotifyDoctor and MinorAlarm) are triggered.

NotifyDoctor and MinorAlarm both are re-evaluated. MinorAlarm becomes true and its parent nodes (NotifyNurse and a nameless NOT) are triggered. The NotifyDoctor node also becomes true so the doctor is notified.

NotifyNurse and the nameless NOT both are re-evaluated. The nameless NOT becomes true and its parent (NurseCannotHelp) is triggered. The node NotifyNurse also becomes true so the nurse is notified.

NurseCannotHelp is re-evaluated and its parent (NotifyDoctor) is triggered so that it is re-evaluated. The node NotifyDoctor becomes false again, which is the correct value given the current input values.

However, the damage is already done: the doctor has already been notified, while only the nurse should have been notified.

When multiple input values change simultaneously, the triggers for these changes can interfere with each other, as shown in the below example.

In the heart monitoring example, it could occur that the Patient.Heartrate drops below the threshold (150) shortly after the Patient.Bloodpressure exceeds the associated threshold (100). For a brief moment, a MajorAlarm condition exists, but it might never be detected if the HeartrateAlarm is re-evaluated before the MajorAlarm is re-evaluated. This is described in the evaluation sequence below:

In the initial state only a HeartrateAlarm (>150) exists (Boolean value true).

Then the Bloodpressure exceeds the threshold (100) and its parent (BloodpressureAlarm) is triggered.

Shortly thereafter, the Patient.Heartrate drops below the threshold (150) and its parent node (HeartrateAlarm) is triggered.

Next, the BloodpressureAlarm is re-evaluated (true) and its parent (MajorAlarm) is triggered.

But before MajorAlarm is re-evaluated, first the HeartrateAlarm is re-evaluated (to false again) and its parent (MajorAlarm) is triggered (again).

Only then is MajorAlarm re-evaluated (to false) and the major alarm condition that existed shortly is never detected.

Note that the above examples only illustrates the problems that can occur. The problem will occur in any expression graph that has parallel paths between two nodes, in which one change causes different reactions in the ancestor.

According to an embodiment of the present invention, the problem of parallel trigger paths can be solved by scheduling the reception of a trigger (in contrast to scheduling the sending of the triggers). Furthermore, each node is assigned a priority that is based on its level in the expression graph. Nodes with a higher priority (=closer to the input values) will receive a trigger earlier than nodes with a lower priority (for the same change!). The consequence is that a node will only receive a trigger after all nodes with a higher priority have received their triggers first. The re-evaluation of a node is hence always based on stable operands and never on unstable ones.

The problem of simultaneous changes can be solved in a further embodiment of the present invention by making a distinction between internal triggers and external triggers. Any change to an input value node is considered an external trigger, whereas changes to all other nodes are considered internal triggers. Now both types of triggers can be scheduled independently. According to an embodiment of the present invention, external triggers are only executed when there are no internal triggers to be executed. Implementation may be accomplished using an internal trigger queue and an external trigger queue. The external trigger queue can be a simple first-in-first-out queue, of which an implementation (hardware or software) is well known to the skilled person. The internal trigger queue is a priority based queue, in which the trigger with the highest priority is executed first. Also for this type of queue, the skilled person is aware of (hardware or software) implementations.

Both mechanisms described above can be combined very well in one scheduling mechanism, where only the internal triggers are scheduled using priorities. In a further embodiment, the two mechanisms are combined for the triggered expression evaluation to work correctly in all possible situations.

An exemplary embodiment of the present invention is now explained using the same expression evaluation described above to illustrate how the problems associated with prior art implementations are prevented.

In order to avoid interference between simultaneous changes, a further exemplary embodiment of the present invention includes that internal triggers are scheduled independently from external triggers. External triggers are only executed when no internal triggers exist.

A straightforward implementation for such a scheduling mechanism is the use of two independent queues: one queue 8 for internal triggers and one queue 7 for external triggers. As long as triggers exist in the internal trigger queue 8 they are executed. Triggers from the external trigger queue 7 are only executed when the internal trigger queue is empty.

An alternative implementation would only use a single queue. External triggers are then assigned the lowest priority available, i.e. lower than all internal triggers, and the internal trigger queue 8 is scheduled on the basis of priorities. This also ensures that external triggers are only scheduled when no internal triggers are in the queue anymore.

Figure 4:
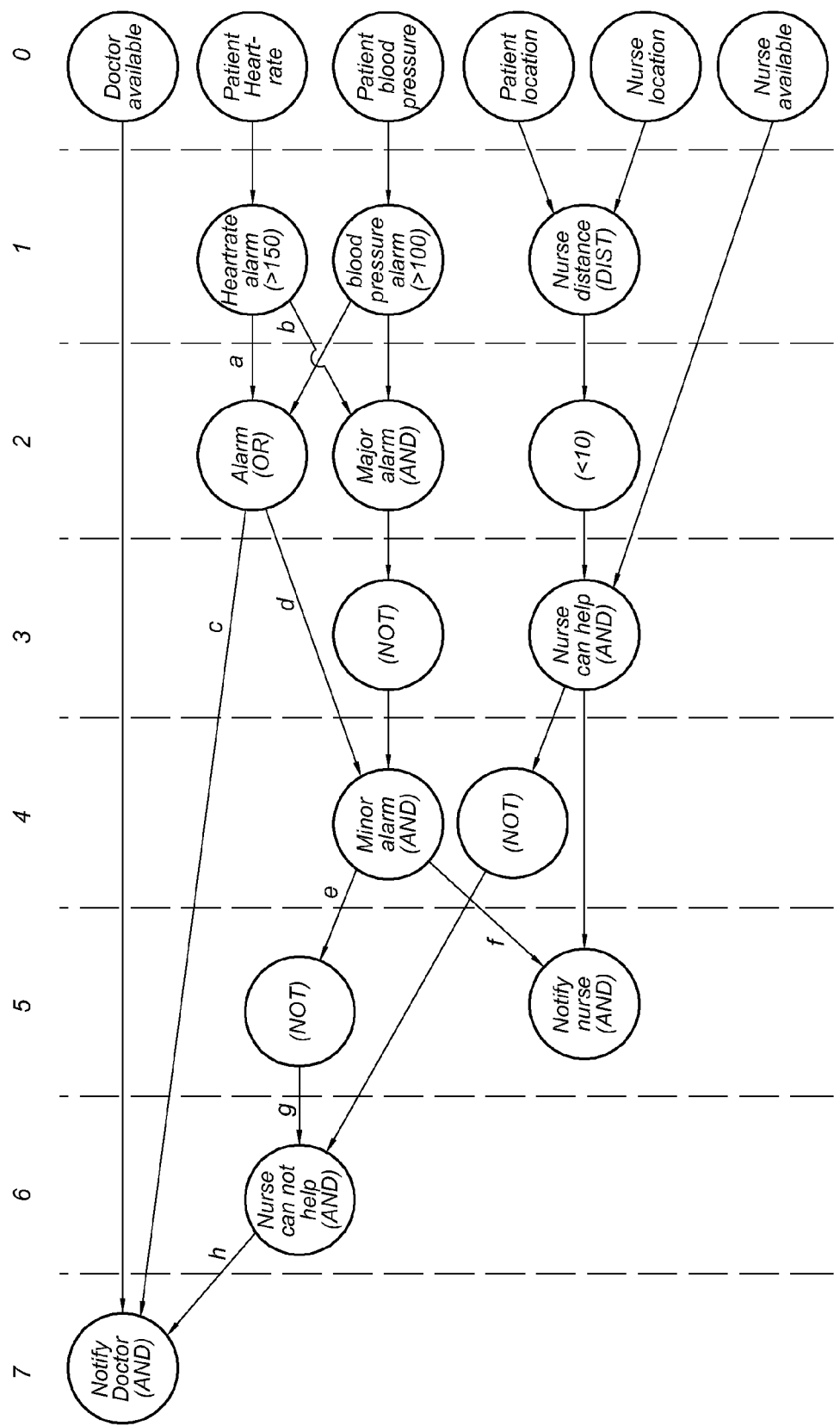
FIG. 4 shows the graph representation of FIG. 2 in which the nodes are assigned levels.

This mechanism is now discussed with the same example as described above, with reference to FIG. 4. In FIG. 4, the graph of FIG. 2 is shown again, but now priorities are assigned to each of the nodes (discussed in detail below), and triggers relevant for the example are numbered from (a) to (h).

First it is shown that the simultaneous change problem is solved:

In the initial state only a HeartrateAlarm is true.

The Patient.Bloodpressure exceeds the threshold (100) and an external trigger (a) is scheduled (entered into external trigger queue).

Shortly thereafter, the Patient.Heartrate drops below the threshold (150) and another external trigger (b) is scheduled (entered in external trigger queue).

The first trigger (a) is executed (from the external trigger queue). The BloodpressureAlarm is re-evaluated (changes to true) and the resulting trigger (c) is scheduled in the internal queue:

ext. queue (b)

int. queue (c)

The next trigger (c) is executed (from the internal trigger queue, as this prevails a trigger from the external trigger queue). The MajorAlarm is re-evaluated and detected to be true.

The next trigger (b) is executed (from the external trigger queue). The HeartrateAlarm is re-evaluated (changes to true) and the resulting trigger (d) is scheduled in the internal queue.

The last trigger (d) is executed (from the internal trigger queue). The MajorAlarm is re-evaluated and detected to be false.

The fundamental difference to the example above illustrating the problem, is the fact that the MajorAlarm correctly changed to true and back to false. The further implications on the top level nodes (up to NotifyDoctor and NotifyNurse nodes) is not included as it is irrelevant for the illustration of the problem solution. The change in MajorAlarm would be undetected without the invention. Note that the temporary value change is correct in this case and should not be confused with the incorrect temporary value change that occurs in the multiple trigger paths problem.

In order to prevent unstable value changes due to multiple paths in the graph representing the expression evaluation, (internal) triggers must be scheduled using priorities based on the level of the node that receives the trigger. Note that this means that a single value change can cause triggers with different priorities, simply because the levels of the receiving parents differ. The different levels are illustrated in FIG. 4 which depicts a rearranged version of the original graph. In the diagram each parent is put one level higher than the highest level of all of its operands.

Note that input values have a level 0 because they do not have any operands. The computation of the levels can be performed using the following algorithm:

```
function calculateLevel(n : Node) : integer
    if n has no operands
```

```
return 0
max = 0
foreach operand of n
    if level of operand > max
        max = level of operand
return max + 1
```

Again, internal triggers are scheduled using an internal trigger queue, a priority queue in this case. Each trigger is inserted in the queue just before the first trigger with a lower priority (=higher level).

The mechanism is illustrated with the same example as above. The HeartrateAlarm is re-evaluated and the resulting triggers (a, b) are scheduled; both have the same priority (level 2) since the receivers are on the same level:

internal trigger queue: (a)/2; (b)/2.

The first trigger (a) is executed. Alarm is re-evaluated (changes to true) and the resulting triggers (c, d) are scheduled; they have different priorities since the receivers are on different levels:

internal trigger queue: (b)/2; (d)/4; (c)/7.

The next trigger (b) is executed. MajorAlarm is re-evaluated, but does not change, hence no triggers are scheduled (i.e. inserted in the internal trigger queue).

The next trigger (d) is executed. MinorAlarm is re-evaluated (changes to true) and the resulting triggers (e, f) are scheduled. Note that they are scheduled before the existing trigger (c) which has a lower priority (=higher level):

internal trigger queue: (e)/5; (f)/5; (c)/7.

The next trigger (e) is executed and the nameless NOT is re-evaluated (changes to false); the resulting trigger (g) is scheduled:

internal trigger queue: (f)/5; (g)/6; (c)/7.

The next trigger (f) is executed and NotifyNurse is re-evaluated and becomes true, so the nurse is notified. No triggers are scheduled.

The next trigger (g) is executed and NurseCannotHelp is re-evaluated (changes to false) and the resulting trigger (h) is scheduled:

internal trigger queue: (c)/7; (h)/7.

When the next trigger (c) is executed NotifyDoctor is re-evaluated and does not change, so no doctor is notified. The same happens when the last trigger (h) is executed (note that the second trigger (h) is superfluous and could be removed during queue optimisation).

The fundamental difference to the similar example without implementation of the present invention is that the node NotifyDoctor never changed to true, hence the doctor is not notified.

In the above examples, both mechanisms may be applied simultaneously, e.g. when during the evaluation last described an input value changes, the external trigger queue is again filled, and is only scheduled after any internal triggers awaiting in the queue.

It will be understood that the present invention may be applied in every implementation of triggered expression evaluation involving (nested) internal expressions and external input values (context sources), such as the service application in a telecommunication network as described above. A further example of an implementation are complex sensor applications, in which multiple sensors are being monitored, and the values thereof are being evaluated using an expression evaluation. Implementations can e.g. be in industrial control systems, or automotive applications.

Figure 5:
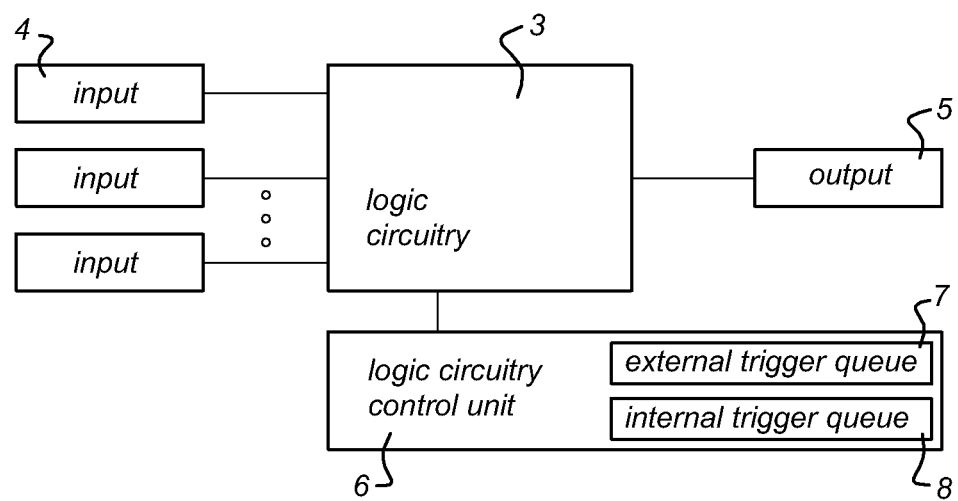
FIG. 5 shows a schematic diagram of an implementation of the present invention in a processing circuit.

FIG. 5 shows a schematic diagram of an implementation of the present invention in a processing circuit. The processing circuit comprises one or more input units 4 and an output unit 5. Logic circuitry 3 is connected to the one or more input units 4 and output unit 5, which the logic circuitry 3 implements a set of logical expressions for expression evaluation. The input units 4 are used to obtain input values and the output unit 5 is used to provide an evaluation result. A logic circuitry control unit 6 is provided for controlling the order of expression evaluation in the set of expressions according to one of the method embodiments as described above. The logic circuitry control unit may be provided with an internal trigger queue 8, and optionally an external trigger queue 7.

The implementation of the method embodiments of the present inventions may be accomplished in hardware (e.g. (programmable) logic circuitry), in software (processor executable instructions, ranging from assembler code to high level programming languages), or combinations thereof.

The invention claimed is:

1. A method for triggered expression evaluation that obtains an evaluation result responsive to a change to an input value of an expression graph having a plurality of internal and external nodes, the method implemented by one or more processing circuits of a computing device and comprising:
    scheduling reception of a trigger by one of the internal nodes based on a priority of the internal node, such that the internal node will only receive the trigger after internal nodes having a higher priority have received their respective triggers; and
    based on the scheduled reception, evaluating the plurality of internal and external nodes in the expression graph to obtain the evaluation result;
    wherein each external node comprises an input value and provides a trigger output to at least one of the internal nodes upon a change of its input value;
    wherein each internal node comprises an expression on one or more operands, each of the one or more operands comprising a trigger from one of the internal or external nodes; and
    wherein the priority of a given internal node is a function of a quantity of internal nodes operatively connected between the given internal node and a most distant external node operatively connected thereto.

2. The method of claim 1,
    wherein an internal node receives its associated operands from one or more sending nodes; and
    wherein the internal node obtains a priority that is lower than a lowest priority of the sending nodes.

3. The method of claim 1, in which an internal queue is used in which a trigger is entered in a prioritized order using the priority of the internal node receiving the trigger.

4. The method of claim 3, in which external triggers are only scheduled when no internal triggers exist.

5. The method of claim 3, in which external triggers are scheduled with a lowest priority.

6. The method of claim 1, in which external triggers are entered in an external trigger queue.

7. The method of claim 1, in which the method is applied for a service provided in a communication network.

8. A network node operative to perform triggered expression evaluation of an expression graph in a communication network, the expression graph having a plurality of internal and external nodes, the network node comprising:
    one or more processing circuits configured to:
        schedule reception of a trigger by one of the internal nodes based on a priority of the internal node, such that the internal node will only receive the trigger after internal nodes having a higher priority have received their respective triggers; and based on the scheduled reception:
evaluate the plurality of internal and external nodes in the expression graph to obtain the evaluation result; and
provide the evaluation result to communication devices in the communication network;

wherein each external node receives an input value from a context source in the communication network and provides a trigger output to at least one of the internal nodes upon a change of its input value;

wherein each internal node comprises an expression on one or more operands, each of the one or more operands comprising a trigger from one of the internal or external nodes; and wherein the priority of a given internal node is a function of a quantity of internal nodes operatively connected between the given internal node and a most distant external node operatively connected thereto.

9. The network node of claim 8, wherein an internal node receives its associated operands from one or more sending nodes, and wherein the one or more processing circuits of the network node are further configured to:
provide the internal node with a priority that is lower than a lowest priority of the sending nodes.

10. The network node of claim 8, in which the network node comprises an internal queue in which a trigger is entered in a prioritized order using the priority of the internal node receiving the trigger.

11. The network node of claim 10, in which external triggers are only scheduled when no internal triggers exist.

12. The network node of claim 10, in which external triggers are scheduled with a lowest priority.

13. The network node of claim 8, in which external triggers are entered in an external trigger queue.

14. A processing circuit operative to implement triggered expression evaluation of an expression graph having a plurality of internal and external nodes, the processing circuit comprising:
one or more input units operative to receive input values;
an output unit operative to provide an output value;
logic circuitry connected to the one or more input units and the output unit and operative to determine the output value based on the input values; and
a control unit operative to control an order of expression evaluation in the expression graph;

wherein the processing circuit is configured to:
schedule reception of a trigger by one of the internal nodes based on a priority of the internal node, such that the internal node will only receive the trigger after internal nodes having a higher priority have received their respective triggers; and
based on the scheduled reception, evaluate the plurality of internal and external nodes in the expression graph to obtain the output value;

wherein each external node comprises an input value and provides a trigger output to at least one of the internal nodes upon a change of its input value;

wherein each internal node comprises an expression on one or more operands, each of the one or more operands comprising a trigger from one of the internal or external nodes; and wherein the priority of a given internal node is a function of a quantity of internal nodes operatively connected between the given internal node and a most distant external node operatively connected thereto.

* * * * *